(12) United States Patent
Moszner et al.

(10) Patent No.: US 7,595,354 B2
(45) Date of Patent: Sep. 29, 2009

(54) DENTAL MATERIALS WITH UNUSUAL FLUORINE DISTRIBUTION

(75) Inventors: Norbert Moszner, Triesen (LI); Urs Karl Fischer, Arbon (CH); Volker M Rheinberger, Vaduz (LI); Giancarlo Galli, Pescia (IT); Marina Ragnoli, Collesalvetti (IT); Emo Chiellini, Pisa (IT)

(73) Assignee: Ivoclar Vivadent AG, Schaan (LI)

( * ) Notice: Subject to any disclaimer, the term of this patent is extended or adjusted under 35 U.S.C. 154(b) by 574 days.

(21) Appl. No.: 11/338,034

(22) Filed: Jan. 24, 2006

(65) Prior Publication Data

US 2006/0287458 A1 Dec. 21, 2006

(30) Foreign Application Priority Data

Jun. 21, 2005 (EP) .................. 05105472

(51) Int. Cl.
- A61C 5/04 (2006.01)
- A61K 6/083 (2006.01)
- C08F 12/20 (2006.01)
- C08F 232/04 (2006.01)

(52) U.S. Cl. .................... 523/116; 523/118; 433/228.1; 526/242; 526/309

(58) Field of Classification Search .................. 523/116, 523/118; 526/242, 309
See application file for complete search history.

(56) References Cited

U.S. PATENT DOCUMENTS

| | | | |
|---|---|---|---|
| 4,616,073 A | 10/1986 | Antonucci et al. | |
| 6,136,887 A | 10/2000 | Moszner et al. | |
| 6,185,339 B1 | 2/2001 | Ozaki | |
| 6,723,376 B1 | 4/2004 | Hamilton et al. | |
| 7,365,222 B2 * | 4/2008 | Moszner et al. ............. | 560/124 |
| 2004/0077882 A1 | 4/2004 | Moszner et al. | |
| 2004/0121168 A1 | 6/2004 | Goodwin et al. | |
| 2005/0043789 A1 | 2/2005 | Widenhouse et al. | |

OTHER PUBLICATIONS

Bertolucci et al., "Wetting Behavior of Films of New Fluorinated Styrene-Siloxane Block Copolymers," *Macromolecules* 37:3666-3672 (2004).
Bongiovanni et al., "High Resolution XPS Investigation of Photocured Films Containing Perfluoropolyether Acrylates," *Polymer* 41:409-414 (2000).
Choi et al., "Novel Polymerization of Fluorinated 2-Vinylcyclopropane in Aqueous Solution via Cyclodextrin Complexes," *Macromol. Chem. Phys.* 204:1475-1479 (2003).
De Meijere et al., "Synthesis and Radical Polymerization of Various 2-Cyclopropylacrylates," *Eur. J. Org. Chem.* 3669-3678 (2004).
Fujmori et al., "Monolayer Assemblies of Comb Polymers Containing Different Kinds of Fluorocarbon Side-Chains," *Macromol. Chem. Phys.* 205:843-854 (2004).

Lee et al., "Synthesis and Surface Properties of Fluorocarbon End-Capped Biodegradable Polyesters," *Macromolecules* 34:3000-3006 (2001).
Lüning et al., "Correlation of Surface and Bulk Order in Low Surface Energy Polymers," *Macromolecules* 34:1128-1130 (2001).
Montefusco et al., "Original Vinylidene Fluoride-Containing Acrylic Monomers as Surface Modifiers in Photopolymerized Coatings," *Macromolecules* 37:9804-9813 (2004).
Moszner et al., "Synthesis and Radical Polymerization of Bi- and Trifunctional 2-Vinylcyclopropanes," *Macromol. Rapid Commun.* 18:775-780 (1997).
Moszner et al., "Synthesis and Radical Polymerization of Methyl 2-(Bicyclo[3.1.0]hex-1-yl)acrylate," *Macromol. Rapid Commun.* 24:269-273 (2003).

(Continued)

*Primary Examiner*—Tae H Yoon
(74) *Attorney, Agent, or Firm*—Nixon Peabody LLP

(57) ABSTRACT

A composition comprising (A) at least one fluorinated vinylcyclopropane according to Formula (I)

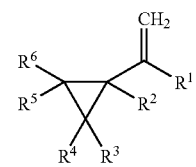

Figure 1:
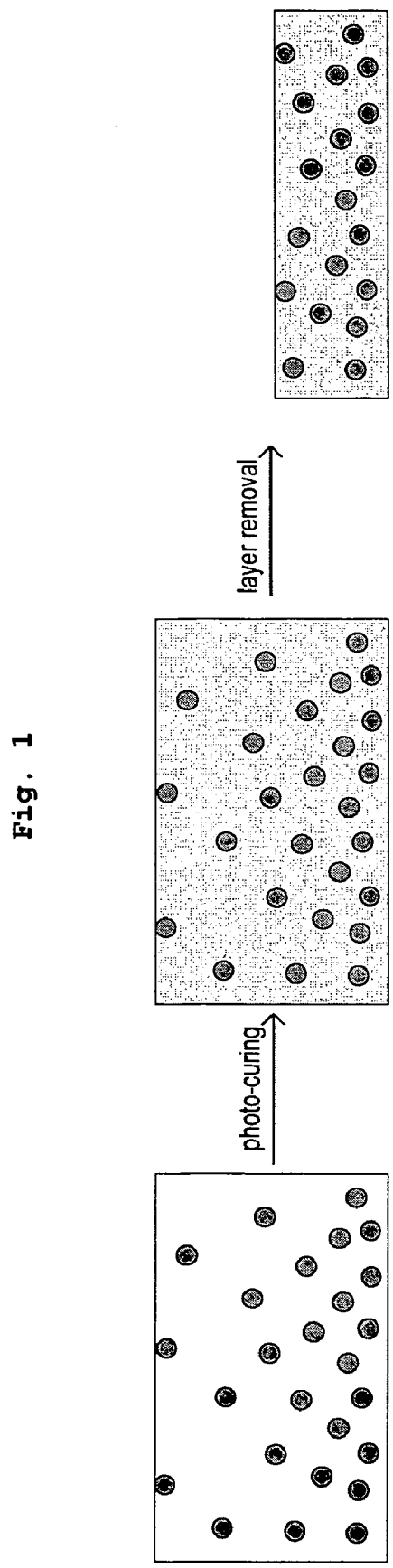

I wherein $R^1$ is H or $-CO-O-(CH_2CH_2)_p-R^7$; $R^2$ is H or forms together with $R^6$ a $-CH_2-C(R^9)(R^{10})-CH_2-$ residue; $R^3$ is H; $R^4$ is H or forms together with $R^5-CH_2-C(R^9)(R^{10})-CH_2-$ residue; $R^5$ is H, $-CO-O-R^8$, $-CO-O-(CH_2CH_2)_p-R^7$ or forms together with $R^4-CH_2-C(R^9)(R^{10})-CH_2-$ residue; $R^6$ is H, $-CO-O-R^8$, $-CO-O-(CH_2CH_2)_p-R^7$ or forms together with $R^2$ a $-CH_2-C(R^9)(R^{10})-CH_2-$ residue; $R^7$ is perfluorinated $C_2-C_{20}$ aliphatic or alicyclic group; $R^8$ is H, phenyl, benzyl, or a linear or branched $C_1-C_{12}$ aliphatic or alicyclic group; $R^9$ is a H, benzoyl, acetyl or a $C_1-C_5$-alkyl group; $R^{10}$H or a $-CO-O-R^8$; p is 1, 2, 3, or 4, provided that the compound of Formula (I) comprises at least one $-CO-O-(CH_2CH_2)_p-R^7$ residue; (B) at least one non-fluorinated vinylcyclopropane derivative; (C) a bisphenol-A-ether di(meth)acrylate according to Formula (II)

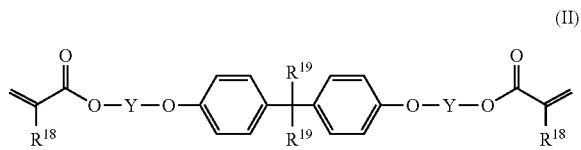

(II)

wherein $R^{18}$ is H or $CH_3$, $R^{19}$ is $CH_3$ or $CF_3$, Y is a $C_2-C_5$-alkylen residue which can be substituted by an OH group or is preferably unsubstituted.

19 Claims, 1 Drawing Sheet

OTHER PUBLICATIONS

Ragnoli et al., "Effects of Chemical Variations on the Mesophase Behavior of New Fluorinated Poly(Vinylcyclopropane)s," *J. Fluorine Chem.* 125:283-292 (2004).

Sankarapandian et al., "Characterization of Some Aromatic Dimethacrylates for Dental Composite Applications," *J. Mater. Sci.: Mater. Med.* 8:465-468 (1997).

Sankarapandian et al., "Synthesis of New Dental Composite Matrix Dimethacrylates," *Amer. Chem. Soc., Polym. Div., Polym. Prepr.*, 38(2):92-93 (1997).

Stansbury & Antonucci, "Dimethacrylate Monomers with Varied Fluorine Contents and Distributions," *Dent. Mater.* 15:166-173 (1999).

Stansbury et al., "Considerations in the Development of Semi-Fluorinated Methacrylate Dental Resins and Composites," *Amer. Chem. Soc., Polym. Div., Polym. Prepr.* 38(2):96-97 (1997).

Stansbury et al., "Photocured Composites Based on Dimethacrylate Monomers of Varied Fluorine Content," *Amer. Chem. Soc., Polym. Div., Polym. Prepr.*, 36(1):831-832 (1995).

Tsibouklis et al., "Poly(perfluoroalkyl methacrylate) Film Structures: Surface Organization Phenomena, Surface Energy Determinations, and Force of Adhesion Measurements," *Macromolecules* 33:8460-8465 (2000).

Van De Grample et al., "Surface Studies of Partially Fluorinated Polymethacrylates: A Combined XPS and LEIS Analysis," *Progr. Org. Coat.* 45:273-279 (2002).

Wang et al., "Physical Property Evaluations of Perfluorothiethylene Glycol Dimethacrylate as a Potential Reactive Diluent in Dental Composite Resins," *J. Macromol. Sci.—Pure Appl. Chem.* A36(2):225-236 (1999).

Wang et al., "Strength, Abrasive Wear, and Durability Properties of Dental Composites Containing a Fluorinate Dimethacrylate Reactive Diluent," *J. Macromol. Sci.—Pure Appl. Chem.* A36(3):373-388 (1999).

Xiang et al., "Surface Stability in Liquid-Crystalline Block Copolymers with Semifluorinated Monodendron Side Groups," *Macromolecules* 33:6106-6119 (2000).

Zeuner et al., "Synthesis and Radical Polymerization of Vinylcyclopropanes," *Macromol. Chem. Phys.* 197:2745-2752 (1996).

Encyclopedia of Polymer Science and Engineering, Wiley-Interscience Pub., John Wiley & Sons, New York, 13:754-776 (1988).

Radiation Curing in Polymer Science and Technology, vol. II, Fouassier & Rabek Pub., Elsevier Applied Science, London (1993) (Cover Page and Table of Contents only).

\* cited by examiner

DENTAL MATERIALS WITH UNUSUAL FLUORINE DISTRIBUTION

The invention primarily relates to material on the basis of fluorinated vinylcyclopropanes which after polymerization show a significant fluorine content in the bulk of the material and not only at the surface thereof. These materials are particularly suitable for dental use.

Fluorinated polymers present unique high-performance properties rendering them particularly attractive for the modification, protection and coating of polymeric and composite materials. Polymers with highly fluorinated side groups have found a number of applications based on the characteristic low surface energy of these materials. They are mainly used in surface technology for the preparation of hydrophobic and oleophobic no-stick coatings in both marine and outdoor environments (T. Hamilton et al. U.S. Pat. No. 6,723,376 B1, G. B. Goodwin et al. US 2004/0121168 A1) and in biomedical systems like antithrombogenic devices (C. W. Widenhouse et al. US 2005/0043789 A1) due to the biocompatibility of fluorine-containing materials.

Typically, low surface energy can be gained even at low contents of fluorine because of the intra- and inter-molecular incompatibility of the fluorocarbon components with hydrocarbon components, with the fluorocarbon analogous compounds having lower surface tension than the respective hydrocarbon analogous compounds. For instance, in a resin matrix that is formulated by mixing various monomers and fillers, the fluorinated monomers tend to migrate to the polymer/air interface driven by their lower surface tension, thus preferentially enriching the outer surface and depleting the bulk of a polymer film. The surface tension of the polymer film is thereby lowered. Diffusion-controlled surface migration and concentration of fluorinated components in a resin are very effective and fast and occur on the time scale of the polymerization of the monomers before the cross-linking and final curing are performed (F. Montefusco et al. Macromolecules, 37, 9804 (2004)).

Fluorine surface enrichment is directly probed by element-sensitive surface spectroscopic techniques. Notable examples include X-Ray Photoelectron Spectroscopy (XPS) (J. Tsibouklis et al. Macromolecules, 33, 8460 (2000)), Localized Electrochemical Impedance Spectroscopy (LEIS) analysis (R. D. van de Grampel et al. Progr. Org. Coat., 45, 273 (2002)), and Near-Edge X-Ray Absorption Fine-Structure Spectroscopy (NEXAFS) (J. Lüning et al. Macromolecules, 34, 1128 (2001)) of variously fluorinated poly(meth)acrylates. All such investigations confirm that there is a concentration gradient normal to the surface across the film thickness by which the outer layers are greatly enriched in fluorine, whereas the inner bulk layers are depleted. Fluorine surface enrichment is also generally evidenced by measurements of contact angles of hydrophobic film surfaces. For example, the preferential residence of fluorinated monomers at the outer surface for cross-linked (meth)acrylate resins incorporating fluorinated monomers was inferred by Stansbury et al. (U.S. Pat. No. 6,185,339 B1) by measurements of much larger water contact angles than for the respective cross-linked (meth)acrylate resins without fluorinated monomers.

Surface enrichment by fluorinated monomer components is well known in the art and occurs in diverse resin formulations irrespective of the chemical structure of the fluorinated component at any composition within its solubility limit in the resin comonomers. For example, poly(vinylidene fluoride) acrylate monomers act as surface modifiers in photocured resin films even at lower concentrations than 0.10 wt. % (F. Montefusco et al. Macromolecules, 37, 9804 (2004)).

Perfluoropolyether acrylates are found to behave like surfactants in photocured polymer networks by concentrating at the polymer/air interface and lower the polymer surface energy (R. Bongiovanni et al. Polymer, 41, 409 (2000)). In all these cases, a cross-linked network structure is formed upon polymerization and the concentration gradient is permanently frozen in the resin, thereby resulting in low surface energy properties.

The tendency of fluorinated constituents to surface segregate and lower the surface tension of the polymer is very distinct and intervenes very effectively for completely different polymeric materials in various configurations, such as diblock or triblock copolymers comprised of a fluorinated polymer block (M. Bertolucci et al. Macromolecules, 37, 3666 (2004)), polyesters with fluorocarbon end groups (W.-K. Lee, Macromolecules, 34, 3000 (2001)), Langmuir monolayers of fluorinated polymers (A. Fujimori et al. Macromol. Chem. Phys., 205, 843 (2004)), and polymers with semifluorinated monodendron side groups (M. Xiang et al. Macromolecules, 33, 6106 (2000)).

Beside the low surface energies, fluorocarbon-containing polymers are highly hydrophobic and display excellent resistance to softening in conjunction with a wide range of chemicals. Furthermore, the potential resistance to staining and microbial attachment, as well as the generally good biocompatibility make fluorinated polymers very attractive for dental application. For example, the new semi-fluorinated BisA-GMA (2,2-bis[4-(2-hydroxy-3-methacryloyloxypropyl)-phenyl]propane) analogues (M. Sankarapandian et al., Amer. Chem. Soc, Polym. Div., Polym. Prepr., 38(2), 92 (1997)) demonstrated a significantly lower viscosity (0.8-1.3 Pa) and exhibited a higher conversion of methacrylate double bonds for the isothermal polymerization at 80° C. Moreover, materials based on these semi-fluorinated BisA-GMA analogues showed a lower water uptake and thus higher Vickers hardness values of water saturated samples compared with BisA-GMA-based materials (M. Sankarapandian et al., J. Mater. Sci.: Mater. Med., 8, 465 (1997)).

Further investigations of the visible-light cured dental materials showed (J. W. Stansbury et al., Amer. Chem. Soc., Polym. Div., Polym. Prepr., 36 (1), 831 (1995); J. W. Stansbury et al., Amer. Chem. Soc., Polym. Div., Polym. Prepr., 38 (2), 96 (1997); J. W. Stansbury et al., Dent. Mater., 15: 166-173 1999)) that, on the one hand, the use of bisphenol A (BisA), or its fluorinated analogue, as a core structure in the monomers provided composites with the highest mechanical strength, while, on the other hand, the placement of fluorine in the extended perfluoroalkyl chains did not decrease the water absorption and resulted in lower mechanical strength compared with the use of alternate fluorinated aromatic terminal groups. An alternative approach to fluorinated BisA-GMA analogues was the use of fluorinated dimethacrylate-reactive diluents, for example, fluorinated triethyleneglycol dimethacrylate which resulted in a decrease in both water absorption and polymerization shrinkage in dental composites (G. Wang et al., J. Macromol. Sci.-Pure Appl. Chem., A36, 225 (1999); G. Wang et al., J. Macromol. Sci.-Pure Appl. Chem., A36, 373 (1999)).

Choi et al., Macromol. Chem. Phys. 2003, 204, 1475-1479, describe the homopolymerization of fluorinated 2-vinylcylopropane and the co-polymerization of fluorinated and non-fluorinated 2-vinylcyclopropanes in aqueous solution via cyclodextrin complexes in the absence of fluorinated co-solvents or surfactants. The polymers prepared exhibited liquid crystal behaviour.

It is known in the art that radical polymerization of monomers in the presence of oxygen results in the formation of a sticky unpolymerized surface layer due to the inhibition of the radical reaction by oxygen. This smear layer is usually removed after the polymerization. Since fluorinated monomers tend to accumulate in the surface layer, they are removed to a large extent together with the smear layer. Furthermore, dental materials are subjected to wear which naturally mainly affects the surface layer. Thus, the content of fluorinated components is further reduced by erosion of the surface layer. As a consequence the positive effects associated with fluorinated monomers are eliminated to a great extent.

It is the object of the present invention to provide compositions which show good water resistance and resistance to staining and microbial attachment after hardening and which at the same time have good mechanical properties.

According to the present invention this object is achieved by compositions comprising
(A) at least one fluorinated vinylcyclopropane according to Formula (I)

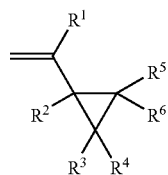

wherein
$R^1$ is H or —CO—O—$(CH_2CH_2)_p$—$R^7$,
$R^2$ is H or forms together with $R^6$ a —$CH_2$—$C(R^9)(R^{10})$—$CH_2$— residue,
$R^3$ is H,
$R^4$ is H or forms together with $R^5$ a —$CH_2$—$C(R^9)(R^{10})$—$CH_2$— residue,
$R^5$ is H, —CO—O—$R^8$, —CO—O—$(CH_2CH_2)_p$—$R^7$ or forms together with $R^4$ a —$CH_2$—$C(R^9)(R^{10})$—$CH_2$— residue,
$R^6$ is H, —CO—O—$R^8$, —CO—O—$(CH_2CH_2)_p$—$R^7$ or forms together with $R^2$ a —$CH_2$—$C(R^9)(R^{10})$—$CH_2$— residue,
$R^7$ is perfluorinated aliphatic or alicyclic $C_2$-$C_{20}$ group,
$R^8$ is H, phenyl, benzyl, or a linear or branched aliphatic or alicyclic $C_1$-$C_{12}$, preferably $C_1$-$C_5$ group,
$R^9$ is a H, benzoyl, acetyl or a $C_1$-$C_5$-alkyl group,
$R^{10}$ H or a —CO—O—$R^8$,
p is 1, 2, 3 or 4,
provided that the compound of formula (I) comprises at least one —CO—O—$(CH_2CH_2)_p$—$R^7$ residue,
(B) at least one non-fluorinated vinylcyclopropane derivative,
(C) at least one bisphenol-A-ether di(meth)acrylate according to formula (II)

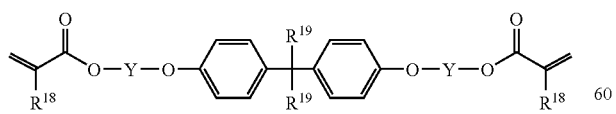

wherein
$R^{18}$ is H or $CH_3$,
$R^{19}$ is $CH_3$ or $CF_3$
Y is a $C_2$-$C_5$-alkylen residue which can be substituted by an OH group or is preferably unsubstituted.

It was surprisingly found that upon hardening of these compositions no surface enrichment of fluorinated monomers occurred. To the contrary, the fluorine concentration in the bulk phase of the hardened compositions was higher than the concentration in the surface area. As a consequence the smear layer which formed upon polymerization in the presence of oxygen can be removed without impairing the desirable properties associated with the use of fluorinated monomers, i.e. good water resistance and resistance to staining and microbial attachment. In addition, the properties of the hardened materials were not impaired by wear.

According to a preferred embodiment of the invention a substance according to formula (I) is used as component A wherein
$R^1$ is H,
$R^2$ is H,
$R^3$ is H
$R^4$ is H,
$R^5$ is —CO—O—$R^8$ and
$R^6$ —CO—O—$(CH_2CH_2)_p$—$R^7$.

These compounds are represented by the following formula Ia:

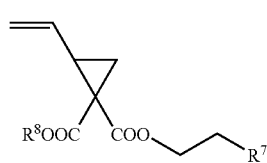

According to another preferred embodiment of the invention a substance according to Formula (I) is used as component A wherein
$R^1$ is —CO—O—$(CH_2CH_2)_p$—$R^7$,
$R^2$ is H or forms together with $R^6$ a —$CH_2$—$C(R^9)(R^{10})$—$CH_2$— residue,
$R^3$ is H
$R^4$ is H or forms together with $R^5$ a —$CH_2$—$C(R^9)(R^{10})$—$CH_2$— residue,
$R^5$ is H or forms together with $R^4$ a —$CH_2$—$C(R^9)(R^{10})$—$CH_2$— residue,
$R^6$ is H or forms together with $R^2$ a —$CH_2$—$C(R^9)(R^{10})$—$CH_2$— residue.

It is preferred that these compounds comprise only one —$CH_2$—$C(R^9)(R^{10})$—$CH_2$— residue. These compounds are represented by formula Ib:

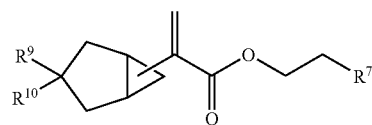

Particularly preferred monomers of this type are compounds according to formulas Ic and Id:

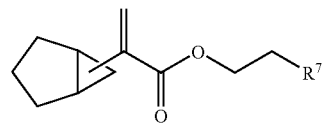

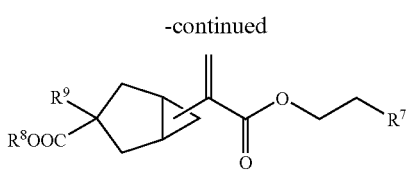

In formulas Ia to Id residues $R^7$ to $R^{10}$ and variable p are as defined above for formula I. Preferably these variables have one of the following meanings, which can be selected independently of each other:

$R^7$ is perfluorinated aliphatic or alicyclic $C_6$-$C_{14}$ group,
$R^8$ is a $C_1$-$C_{12}$, preferably $C_1$-$C_5$ alkyl group,
$R^9$ is a H, benzoyl or acetyl,
$R^{10}$ H or a —CO—O—$R^8$,
p is 1.

Component (B) is preferably a vinylcyclopropane derivative selected from the group consisting of vinylcyclopropanes according to Formula (III) and bicyclo[3.1.0]hexanes according to Formulas (IV) and (V)

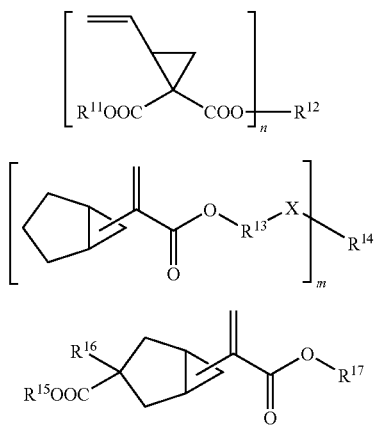

$R^{11}$ is H, phenyl, benzyl, or a $C_1$-$C_{10}$ alkyl group,
$R^{12}$ is an aliphatic or alicyclic $C_1$-$C_5$ group or a $C_6$-$C_{14}$ aryl group which is n-fold substituted by the group in brackets,
$R^{13}$ is a $C_1$-$C_{10}$ alkylene group which may be interrupted by O or is absent,
$R^{14}$ is an aliphatic or alicyclic $C_1$-$C_{15}$ alkyl group or a $C_6$-$C_{14}$ aryl group which is m-fold substituted by the group in brackets,
$R^{15}$ is H, phenyl, benzyl, or a $C_1$-$C_{10}$ alkyl group,
$R^{16}$ H, benzoyl, acetyl, or a $C_1$-$C_5$ alkyl group,
$R^{17}$ is H, phenyl, benzyl, or a $C_1$-$C_{10}$ alkyl group,
X is O, NH or is absent, X being absent if $R^{13}$ is absent,
m is 1, 2 or 3,
n is 1, 2 or 3.

The variables of formulae III, IV and V preferably have the following meanings, which can be selected independently of each other:

$R^{11}$ is benzyl or a $C_1$-$C_5$ alkyl group,
$R^{12}$ is an aliphatic or alicyclic $C_3$-$C_{10}$ alkyl group or a phenyl group which is n-fold substituted by the group in brackets,
$R^{13}$ is absent,
$R^{14}$ is an aliphatic or alicyclic $C_3$-$C_{10}$ alkyl group or a phenyl group which is m-fold substituted by the group in brackets,
$R^{15}$ is a $C_1$-$C_5$ alkyl group,
$R^{16}$ H, benzoyl or acetyl,
$R^{17}$ is a $C_1$-$C_5$ alkyl group,
X is absent,
n is 1,
m is 1.

The variables of formula II have the following preferred meanings which can be selected independently of each other:

$R^{18}$ is $CH_3$,
$R^{19}$ is $CH_3$ or $CF_3$
Y is methylethylene.

In the above formulas alkyl can be a branched or preferably a linear group. Preferred aliphatic groups are alkyl groups, preferred alicyclic groups are cycloalkyl groups.

If the compounds of the above formulas contain several radicals of one type, for example several $R^7$ radicals, these can be identical or different.

The above formulas cover all the constitutional and stereoisomeric forms and mixtures of different constitutional and stereoisomeric forms, such as e.g. racemates. As can be seen from the above formulae, the radicals —C(=$CH_2$)—C(=O)—O—R can be bonded to the cyclopropane ring via the bridge atom or preferably a bridgehead atom. The formula covers only compounds which are consistent with the chemical valence theory.

The feature that a radical can be interrupted by foreign atoms, such as oxygen, is to be understood to mean that one or more of the foreign atoms are integrated into a carbon chain. It follows from this that the foreign atoms cannot be terminal, i.e. binding to neighbouring groups always takes place via a carbon atom, and that the number of foreign atoms must necessarily be smaller than the number of carbon atoms.

The vinylcyclopropanes according to formula I are easily accessible by esterification of the corresponding vinylcyclopropane carboxylic acids with suitable perfluorinated alcohols.

For instance, vinylcyclopropanes according to formula Ia can be prepared as follows:

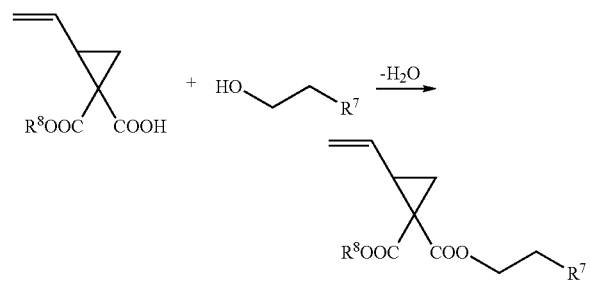

A specific example is the esterification of 1-ethoxycarbonyl-2-vinylcyclopropanecarboxylic acid (N. Moszner, F. Zeuner, V. Rheinberger, Macromol. Rapid Commun. 18, 775 (1997)) with 1H,1H,2H,2H-perfluorododecanol which is commercially accessible (Fluorochem.) to give 1-ethoxycarbonyl-1-[(1H,1H,2H,2H)-perfluorododecyl]-oxycarbonyl-2-vinylcyclopropane (S. W. Choi, O. Kretschmann, H. Ritter, M. Ragnoli, G. Galli, Macromol. Chem. Phys., 204, 1475 (2003)):

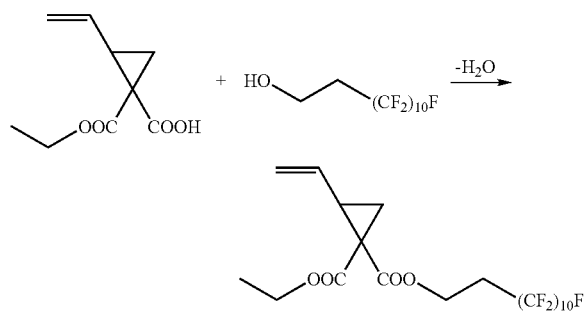

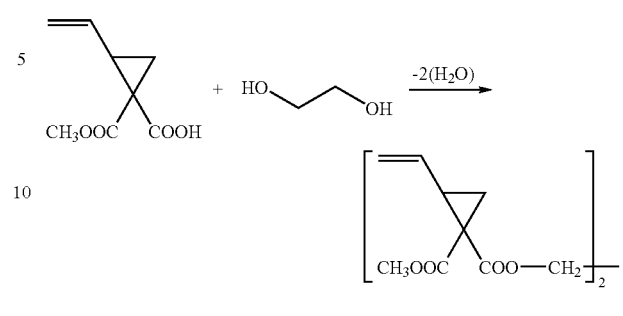

Vinylcyclopropanes according to formulas III, IV and V are accessible by syntheses known from literature.

1,1-Disubstituted 2-vinylcyclopropanes according to formula III (n=1) can be prepared by reaction of the corresponding malonyl diesters with trans-1,4-dibromo-2-butene (F. Zeuner, N. Moszner, V. Rheinberger, Macromol. Chem. Phys., 197, 2745 (1996)):

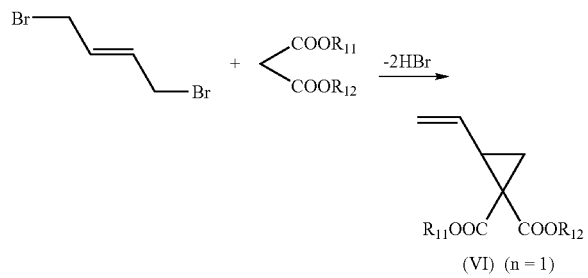

Specific example:

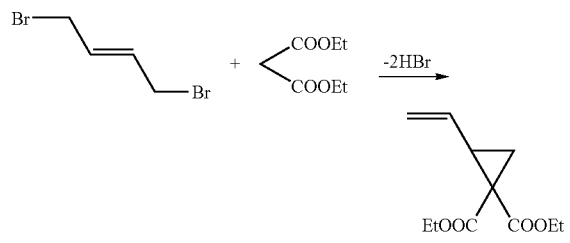

Multifunctional 1,1-disubstituted 2-vinylcyclopropanes according to formula (III) are accessible by esterification of the corresponding vinylcyclopropane carboxylic acids with suitable polyhydroxyl compounds (N. Moszner, F. Zeuner, V. Rheinberger, Macromol. Rapid Commun., 18, 775 (1997)):

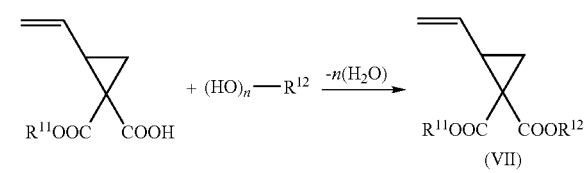

Specific example:

Examples for the synthesis of bicyclic cyclopropylacrylates are reported in the following publications: N. Moszner, F. Zeuner, U. K. Fischer, V. Rheinberger, A. de Meijere, V. Bagutski, Macromol. Rapid Commun., 24, 269 (2003) and A. de Meijere, V. Bagutski, F. Zeuner, U. K. Fischer, V. Rheinberger, N. Moszner, Eur. J. Org. Chem., 3669 (2004).

Propoxylated bisphenol-A-di(meth)acrylate (2,2-bis-[(4-(2-methacryloyloxypropyl)-phenyl)propane, formula (II), $R^{19}=CH_3$) can be synthesized in analogy to the known ethoxylated bisphenol-A-di(meth)acrylates (DE 1 921 869) by esterification of the corresponding diol with (meth)acrylic acid or by transesterification with methyl(meth)acrylate. Accordingly, 2,2-bis-[(4-(2-methacryloyloxypropyl)phenyl)-1, 1,1,3,3,3-hexafluoropropane (formula (II), $R^{19}=CF_3$) can be synthesized by esterification or transesterification of propoxylated 2,2-bis(4-hydroxyphenyl)-1,1,1,3,3, 3-hexafluoro-propane.

The composition of the present invention preferably also contains an initiator for the radical polymerization. The cyclopropyl acrylates according to the invention can be polymerized with known radical initiators (cf. Encyclopedia of Polymer Science and Engineering, Vol. 13, Wiley-Intersci. Pub., New York etc. 1988, 754ff.) accompanied by ring-opening. Preferred initiators for the radical polymerization are azo compounds, such as 2,2'-azobis(isobutyronitrile) (AIBN) or azobis-(4-cyanovaleric acid) or more preferably peroxides, such as dibenzoylperoxide, di-lauroylperoxide, tert.-butylperoctoate, tert.-butylperbenzoate or di-(tert.-butyl)-peroxide.

As initiators for the hot-curing benzopinacol and 2,2'-dialkylbenzopinacols are particularly suitable.

Moreover, photoinitiators (cf. J. P. Fouassier, J. F. Rabek (Publ.), Radiation Curing in Polymer Science and Technology, Vol. II, Elsevier Applied Science, London and New York 1993) can also be used for the UV or visible region, such as benzoin ethers, dialkylbenzilketals, dialkoxyacetophenones, acyl or bisacyl phosphinic oxides, α-diketones such as 9, 10-phenanthrenequinone, diacetyl, furil, anisil, 4, 4'-dichlorobenzil, 4,4'-dialkoxybenzil and camphorquinone. Camphorquinone and 2,2-dimethoxy-2-phenyl-acetophenone are preferably used, more preferably α-diketones, such as camphorquinone, in combination with amines as reductants, such as e.g. 4-(N,N-dimethylamino)-benzoic acid ester, N,N-dimethylaminoethyl methacrylate, N,N-dimethyl-sym.-xylidine or triethanolamine. In addition acylphosphines such as e.g. 2,4,6-trimethylbenzoyldiphenyl- or bis(2,6-dichlorobenzoyl)-4-n-propyl phosphinic oxide are also particularly suitable.

As initiators for a polymerization carried out at room temperature, redox-initiator combinations, such as e.g. combinations of benzoyl or lauroyl peroxide with N,N-di-methyl-sym.-xylidine or N,N-di-methyl-p-toluidine, are used.

In addition, redox systems consisting of peroxides and reductants, such as e.g. ascorbic acid, barbiturates or sulphinic acids, are suitable.

Moreover the compositions used according to the invention can contain fillers, preferably organic or more preferably inorganic particles for improving the mechanical properties, reducing polymerization shrinkage or setting the viscosity. The filler particles preferably have an average particle size of 0.005 to 1.5 µm, more preferably of 0.01 to 1 µm. Preferred inorganic particulate fillers are amorphous spherical materials based on oxides, such as $ZrO_2$ and $TiO_2$ or mixed oxides of $SiO_2$, $ZrO_2$ and/or $TiO_2$, nanoparticulate fillers and minifillers. By nanoparticulate fillers is meant fillers with a primary particle size of approximately 5 to 100 nm, such as pyrogenic silica or precipitated silica. Likewise, minifillers, i.e. fillers with a particle size between 0.1 and 1.5 µm, such as e.g. finely ground quartz, glass ceramic or glass powder, and X-ray-opaque fillers, such as ytterbium trifluoride, nanoparticulate tantalum(V) oxide or barium sulphate, are preferably used as inorganic particulate fillers.

In addition the compositions according to the invention can if required contain further components, such as e.g. stabilizers, UV absorbers, colorants and/or pigments.

The compositions according to the invention are particularly suitable as dental materials, in particular as dental coating materials, dental composites such as fixing cements or filling materials. In contrast to known materials on the basis of fluorinated monomers, the materials of the present invention are characterized by a high fluorine content in the bulk phase and a relatively low fluorine concentration in the surface layer. This is a particular advantage for dental use since the smear layer formed upon hardening of the compositions in the presence of oxygen can be removed without impairing the advantages associated with the use of fluorinated monomers. After hardening and removal of the smear layer the compositions still show good water resistance, little water uptake, high resistance to staining and microbial attachment such as plaque formation.

In addition, the compositions of the invention have small polymerization shrinkage and very good mechanical properties after curing.

The compositions of the present invention preferably comprise 0.1 to 20% by weight, preferably 1.0 to 15% by weight of component (A), 1.0 to 30% by weight, preferably 1.0 to 15% by weight of component (B), 1.0 to 45% by weight, preferably 5.0 to 40% by weight of component (C), 0.01 to 5% by weight, preferably 0.1 to 2.0% by weight initiator.

If not stated otherwise all percentages are by weight and based on the total weight of the composition.

The above composition may additionally comprise 0 to 25% by weight of filler. Such a composition is particularly suitable as a coating material.

Compositions Comprising 0.1 to 15% by weight, preferably 1.0 to 10% by weight of component (A), 1.0 to 20% by weight, preferably 1.0 to 10% by weight of component (B), 1.0 to 40% by weight, preferably 5.0 to 30% by weight of component (C), 0.01 to 5% by weight, preferably 0.1 to 2.0% by weight initiator, 20 to 60% by weight, preferably 30 to 60% by weight filler are particularly suitable as cement.

Composition Comprising 0.1 to 10% by weight, preferably 1.0 to 10% by weight of component (A), 1.0 to 20% by weight, preferably 1.0 to 10% by weight of component (B), 1.0 to 40% by weight, preferably 5.0 to 30% by weight of component (C), 0.01 to 5.0% by weight, preferably 0.1 to 2.0% by weight initiator, 35 to 85% by weight, preferably 40 to 80% by weight filler, are particularly suitable as filling materials.

The compositions of the present invention can be used for forming or coating articles, in particular for forming or coating dental products, such as dental fillings, inlays, onlays, crowns and bridges, veneers or artificial teeth.

Such articles or coated articles can be prepared by a method comprising the steps of shaping composition according to the invention into a body having the desired form or coating a body with a composition according to the invention, hardening the shaped composition and removing the outer layer of the hardened body.

In the following the invention will be further explained with reference to a FIGURE and examples.

FIG. 1 is a schematic diagram showing the fluorine distribution in preferred compositions according to the invention. The first picture shows the fluorine distribution of the uncured material. The fluorine atoms are schematically represented by dark circles. This fluorine distribution of the uncured material is maintained during curing of the material (second picture). After removal of the surface layer e.g. by wear the surface layer comprises even more fluorine atoms than before (third picture).

EXAMPLES

Example 1

1-Ethoxycarbonyl-1-(1H,1H,2H,2H)-perfluoro-dodecyl)oxycarbonyl)-2-vinylcyclopropane (VCP F10)

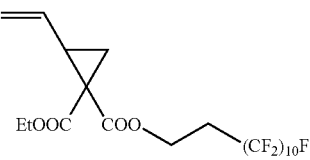

A solution of 22.00 g (39 mmol) of 1H,1H,2H,2H-perfluorododecanol, 7.20 g (39 mmol) of 1-ethoxycarbonyl-2-vinylcyclopropane-1-carboxylic acid and 1.60 g (11 mmol) of 4-dimethylaminopyridine in 75 ml of anhydrous dichloromethane was cooled to 0° C. under a nitrogen atmosphere. Then 8.10 g (39 mmol) of 1,3-dicyclohexylcarbodiimide in 25 ml of anhydrous dichloromethane were slowly added. The mixture was kept under stirring at room temperature for 3 days. The precipitate formed during the reaction was filtered off and the organic solution was extracted with 5% HCl, 5% $Na_2CO_3$ and dried over $Na_2SO_4$. Successively, the solvent was evaporated under vacuum and the crude product was purified by silica gel column flash chromatography (230-400 mesh), using ethyl acetate/n-hexane (1:4 v/v) as eluent (Rf=0.57) to give 18.31 g (64% yield) of VCP-F10 as a pale yellow and transparent liquid.

$^1$H NMR (CDCl$_3$): δ(ppm)=5.4-5.2 (m, 3H, CH$_2$=CH), 4.4 (m, 2H, COO—CH$_2$—CH$_2$), 4.2 (q, 2H, CH$_2$—CH$_3$), 2.5 (m, 3H, CH$_2$—CF$_2$+CH cyclopropane), 1.6-1.7 (2dd, 2H, CH$_2$ cyclopropane), 1.2 (t, 3H, CH$_3$).

FT-IR (liquid film): 3092 (νC—H vinylic), 2986 (νC—H aliphatic), 1734 (νC=O), 1640 (νC=C), 1468 and 1446 (δC—H cyclo), 1350-1120 (δ C—H vinylic, ν C—O ester, ν C—F), 930 (γ C—H vinylic), 656 cm$^{-1}$ (ω CF$_2$).

Example 2

Propoxylated bisphenol AF (p. BisAF)

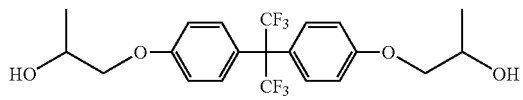

A solution of 33.62 g (100 mmol) of 2,2-bis[4-(hydroxy)phenyl]-1,1,1,3,3,3-hexafluoropropane in 70 ml of tetrahydrofuran and 20 ml of water and 1.60 g (40 mmol) of NaOH was stirred at room temperature until it was homogeneous and 23.20 g (331 mmol) of propylene oxide was added. The reaction was carried out at 50° C. and 10 atm of nitrogen atmosphere for 24 hours. Then HCl was added to neutrality and the organic layer separated from the aqueous one was evaporated under vacuum. The crude residue was dissolved in diethyl ether, washed with water and dried over Na$_2$SO$_4$. Successively, the solvent was evaporated under vacuum and 43.68 g (94% yield) of p. BisAF as a viscous pale yellow liquid was collected.

$^1$H-NMR (CDCl$_3$): δ (ppm)=7.3-6.9 (2d, 8H, aromatic), 4.2 (m, 2H, CH), 3.9 (m, 4H, CH$_2$), 2.7 (s, 2H, OH), 1.3 (d, 6H, CH$_3$).

Example 3

Propoxylated bisphenol-F dimethacrylate (p. BisAF-MA)

A solution of 25.89 g (57 mmol) of p. BisAF and 17.34 g (172 mmol) of triethylamine in 80 ml of anhydrous THF was cooled to 0° C. Then a solution of 17.78 g (172 mmol) of methacryloyl chloride in 20 ml of THF was added dropwise and the mixture was stirred at room temperature for 3 days. The solvent was then evaporated under vacuum, and the residue was dissolved with dichloromethane, washed with 5% HCl, 5% Na$_2$CO$_3$, and water and dried over Na$_2$SO$_4$. Successively, the solvent was evaporated under vacuum and 23.87 g (76% yield) of p. BisAF-MA as a viscous, pale yellow transparent liquid was collected.

$^1$H-NMR (CDCl$_3$): δ (ppm)=7.3-6.9 (2d, 8H, aromatic), 6.1 and 5.6 (s, 4H, CH$_2$=), 5.3 (m, 2H, CH), 4.1 (m, 4H, CH$_2$—OPh), 1.9 (s, 6H, CH$_3$ methacrylate), 1.4 (s, 6H, CH$_3$—CH).

Example 4

Preparation and Characterization of Dental Filling Materials

Corresponding to Table 1 below, various filling materials on the basis of monomers, fillers and photo initiators were prepared by means of an "Exakt" three roll mill (Exakt Apparatebau, Norderstedt).

Testpieces were prepared from materials specified in Table 1, which were cured by being irradiated twice for 3 minutes, by a dental light source (Spectramat®; Ivoclar Vivadent AG).

XPS measurements allowed evaluation of the surface chemical composition of the resins described in the Table 1. It is evident that Composites C-D and C-E contained less fluorine at the surface than in bulk (stoichiometric). Therefore in dental resins C-D and C-E the bulk is fluorine-enriched, whereas the surface is depleted (FIG. 1).

TABLE 1

Composition of dental filling materials C-A to C-E (wt %)

| Component | C-A[a] | C-B[a] | C-C[a] | C-D | C-E |
|---|---|---|---|---|---|
| UDMA | 29.00 | — | — | — | — |
| BisA-GMA | — | 29.05 | — | — | — |
| BisAF-GMA | — | — | 30.85 | — | — |
| VCP-F10 | 8.05 | 8.05 | 6.70 | 8.07 | 6.94 |
| VCP-DE | 2.40 | 2.35 | 1.90 | 2.33 | 2.00 |
| p.BisA-MA | — | — | — | 29.02 | — |
| p.BisAF-MA | — | — | — | — | 30.48 |
| F1 | 41.35 | 41.35 | 41.35 | 41.36 | 41.36 |
| F2 | 18.75 | 18.75 | 18.75 | 18.75 | 18.75 |
| PI | 0.45 | 0.45 | 0.45 | 0.47 | 0.47 |

[a]comparative example

Monomers:

UDMA: Urethane dimethacrylate of 2 mol 2-hydroxyethylmethacrylate and 1 mol 2,2,4-trimethylhexa-methylendiisocyanate (comparative monomer)

BisA-GMA: 2,2-Bis[4-(2-hydroxy-3-methacryloyloxypropyl)-phenyl]propane (comparative monomer)

BisAF-GMA: 2,2-Bis[4-(2-hydroxy-3-methacryloyloxypropyl)-phenyl]-1,1,1,3,3,3-hexafluoropropane (comparative monomer)

VCP-F10: 1-Ethoxycarbonyl-1-(1H,1H,2H,2H)-perfluorodo-decyl)oxycarbonyl)-2-vinylcyclopropane (VCP F10) (Example 1)

VCP-DE: 1,1-Diethoxycarbonyl-2-vinylcyclopropane p.BisA-MA: 2,2-Bis-[(4-(2-methacryloyloxypropyl)phenyl)-propane p.BisAF-MA: 2,2-Bis-[(4-(2-methacryloyloxypropyl)phenyl)-1, 1,1,3,3,3-hexafluoropropane (Example 3)

Fillers:

F1: pyrogenic silica OX-50 (Degussa)

F2: Ytterbium trifluoride (Rhone-Poulenc)

Photoinitiator:

PI: 1:1 (wt/wt) mixture of camphorquinone and N,N-diethyl-3,5-ditertbutylaniline

TABLE 2

| Surface fluorine atomic compositions by XPS | | | | | |
|---|---|---|---|---|---|
| F-Content (%) | C-A | C-B | C-C | C-D | C-E |
| Calculated[a] | 8.53 | 17.91 | 7.73 | 8.15 | 18.78 |
| Experimental | 26.41 | 26.03 | 26.73 | 5.66 | 11.39 |

[a] Calculated on the basis of the composition of the composites under the assumption of homogenous monomer distribution The results show that formulations C-D and C-E allowed to obtain moulds with fluorine amounts at the surface lower than in the bulk, in contrast to the well known tendency of the fluorinated molecules to migrate or segregate to the outer layer and deplete the bulk of the material containing them.

After cross-linking by photo-polymerization of a dental resin in the mouth, dentists remove a relatively thick layer of polymeric material, thereby exposing the inner layers to the oral cavity. After this treatment, the effective surface of a surface-segregated fluorinated resin has the same composition as the depleted bulk and cannot provide the anticipated benefits of fluorinated resins with a high fluorine concentration in the outer layer. Therefore, the unusual phenomenon of fluorine enrichment in the bulk phase of the present invention allows to achieve the properties of highly fluorinated surfaces after the removal of the outer layer (FIG. 1).

Furthermore, the bending strength and the bending E modulus of the cured testpieces were determined in a three-point bending test according to ISO 4049 after 24 hours water storage at 37° C., 24 hours storage in air at room temperature and seven days water storage at 37° C. The results are shown in Table 3.

TABLE 3

| Flexural strength (FS) and flexural modulus of elasticity (FM) of materials C-A to C-E | | | | | |
|---|---|---|---|---|---|
| Property | C-A | C-B | C-C | C-D | C-E |
| FS, air 24 h (MPa) | 86 | 70 | 68 | 75 | 52 |
| FS, water 24 h (MPa) | 85 | 71 | 56 | 68 | 50 |
| FS, water 7 d (MPa) | 87 | 72 | 66 | 61 | 49 |
| FM, air 24 h (GPa) | 4.51 | 5.40 | 5.32 | 4.66 | 3.70 |
| FM, water 24 h (GPa) | 4.17 | 5.26 | 4.14 | 4.41 | 3.61 |
| FM, water 7 d (GPa) | 4.19 | 5.70 | 5.17 | 4.20 | 3.57 |

Linear polymerization shrinkage of the materials was determined on layers having a thickness of 1.8 mm at irradiation with blue light (Astralis® 10 blue light lamp, Ivoclar Vivadent AG) (Table 4).

TABLE 4

| Linear shrinkage (μm) of materials C-A to C-E | | | | | |
|---|---|---|---|---|---|
| | C-A | C-B | C-C | C-D | C-E |
| Linear shrinkage | 35.0 | 30.2 | 28.9 | 32.2 | 30.1 |

The invention claimed is:

1. A composition comprising
(A) at least one fluorinated vinylcyclopropane according to formula (I)

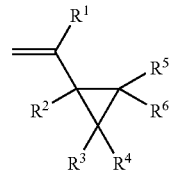

wherein
$R^1$ is H or —CO—O—$(CH_2CH_2)_p$—$R^7$,
$R^2$ is H or forms together with $R^6$ a —$CH_2$—$C(R^9)(R^{10})$—$CH_2$— residue,
$R^3$ is H,
$R^4$ is H or forms together with $R^5$ a —$CH_2$—$C(R^9)(R^{10})$—$CH_2$— residue,
$R^5$ is H, —CO—O—$R^8$, —CO—O—$(CH_2CH_2)_p$—$R^7$ or forms together with $R^4$ a —$CH_2$—$C(R^9)(R^{10})$—$CH_2$— residue,
$R^6$ is H, —CO—O—$R^8$, —CO—O—$(CH_2CH_2)_p$—$R^7$ or forms together with $R^2$ a —$CH_2$—$C(R^9)(R^{10})$—$CH_2$— residue,
$R^7$ is perfluorinated aliphatic or alicyclic $C_2$-$C_{20}$ group,
$R^8$ is H, phenyl, benzyl, or a linear or branched aliphatic or alicyclic $C_1$-$C_{12}$ group,
$R^9$ is a H, benzoyl, acetyl or a $C_1$-$C_5$-alkyl group,
$R^{10}$ is H or a —CO—O—$R^8$, and
p is 1, 2, 3, or 4,
provided that the compound of formula (I) comprises at least one —CO—O—$(CH_2CH_2)_p$—$R^7$ residue,
(B) at least one non-fluorinated vinylcyclopropane, and
(C) at least one bisphenol-A-ether di(meth)acrylate according to formula (II)

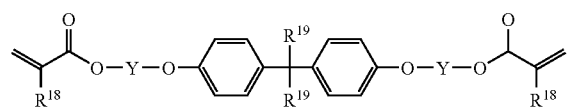

wherein
$R^{18}$ is H or $CH_3$,
$R^{19}$ is $CH_3$ or $CF_3$, and
y is a $C_2$-$C_5$-alkylen residue which is substituted by an OH group or is unsubstituted.

2. The composition of claim 1, wherein
$R^1$ is H,
$R^2$ is H,
$R^3$ is H,
$R^4$ is H,
$R^5$ is —CO—O—$R^8$, and
$R^6$ is —CO—O—$(CH_2CH_2)_p$—$R^7$.

3. The composition of claim 1, wherein
$R^1$ is —CO—O—$(CH_2CH_2)_p$—$R^7$,
$R^2$ is H or forms together with $R^6$ a —$CH_2$—$C(R^9)(R^{10})$—$CH_2$— residue,
$R^3$ is H,
$R^4$ is H or forms together with $R^5$ a —$CH_2$—$C(R^9)(R^{10})$—$CH_2$— residue,
$R^5$ is H or forms together with $R^4$ a —$CH_2$—$C(R^9)(R^{10})$—$CH_2$— residue, and
$R^6$ is H or forms together with $R^2$ a —$CH_2$—$C(R^9)(R^{10})$—$CH_2$— residue.

4. The composition of claim 1, wherein
$R^7$ is perfluorinated aliphatic or alicyclic $C_6$-$C_{14}$ group,
$R^8$ is a aliphatic or alicyclic $C_1$-$C_5$ group,
$R^9$ is a H, benzoyl or acetyl,
$R^{10}$ is H or a —CO—O—$R^8$, and
p is 1.

5. The composition of claim 1, wherein component (B) is a vinylcyclopropane selected from the group consisting of vinylcyclopropanes according to Formula (III) and bicyclo [3.1.0]hexanes according to Formulas (IV) and (V)

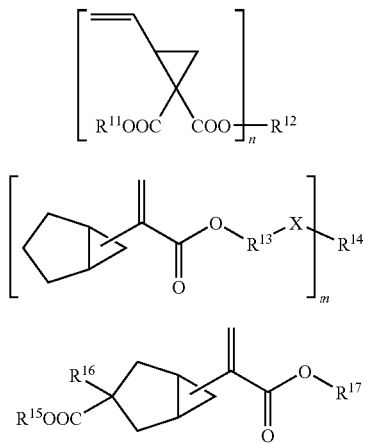

wherein
$R^{11}$ is H, phenyl, benzyl, or a $C_1$-$C_{10}$ alkyl group,
$R^{12}$ is an aliphatic or alicyclic $C_1$-$C_{15}$ group or a $C_6C_{14}$ aryl group which is n-fold substituted by the group in brackets,
$R^{13}$ is a $C_1$-$C_{10}$ alkylene group optionally interrupted by O or is absent,
$R^{14}$ is an aliphatic or alicyclic $C_1$-$C_{15}$ alkyl group or a $C_6$-$C_{14}$ aryl group which is m-fold substituted by the group in brackets,
$R^{15}$ is H, phenyl, benzyl, or a $C_1$-$C_{10}$ alkyl group,
$R^{16}$ is H, benzoyl, acetyl, or a $C_1$-$C_5$ alkyl group,
$R^{17}$ is H, phenyl, benzyl, or a $C_1$-$C_{10}$ alkyl group,
X is O, NH or is absent, X being absent if $R^{13}$ is absent,
n is 1, 2 or 3, and
m is 1, 2 or 3.

6. The composition of claim 5, wherein
$R^{11}$ is benzyl or a $C_1$-$C_5$ alkyl group,
$R^{12}$ is an aliphatic or alicyclic $C_3$-$C_{10}$ alkyl group or a phenyl group which is n-fold substituted by the group in brackets,
$R^{13}$ is absent,
$R^{14}$ is an aliphatic or alicyclic $C_3$-$C_{10}$ alkyl group or a phenyl group which is m-fold substituted by the group in brackets,
$R^{15}$ is a $C_1$-$C_5$ alkyl group,
$R^{16}$ is H, benzoyl or acetyl,
$R^{17}$ is a $C_1$-$C_5$ alkyl group,
X is absent,
n is 1, and
m is 1.

7. The composition of claim 1, wherein
$R^{18}$ is $CH_3$,
$R^{19}$ is $CH_3$ or $CF_3$, and
Y is methylethylene.

8. The composition of claim 1, further comprising an initiator for the radical polymerization.

9. The composition of claim 8, comprising
0.1 to 20% by weight of component (A),
1.0 to 30% by weight of component (B),
1.0 to 45% by weight of component (C), and
0.01 to 5% by weight of initiator for the radical polymerization,
each based on the total weight of the composition.

10. The composition of claim 9, comprising
0.1 to 15% by weight of component (A),
1.0 to 20% by weight of component (B),
1.0 to 40% by weight of component (C),
0.01 to 5.0% by weight initiator, and
20 to 60% by weight filler,
each based on the total weight of the composition.

11. The composition of claim 9, comprising
0.1 to boo by weight of component (A),
1.0 to 20% by weight of component (B),
1.0 to 40% by weight of component (C),
0.01 to 5.0% by weight initiator, and
35 to 85% by weight filler,
each based on the total weight of the composition.

12. The composition of claim 1 further comprising at least one component selected from the group consisting of stabilizers, UV absorbers, colorants and pigments.

13. An article made from or coated with the composition of claim 1.

14. The article of claim 13 having the form of a dental restoration.

15. A method for manufacturing an article comprising the steps of shaping a composition according to claim 1 into a body having the desired form, hardening the shaped composition and removing the outer layer of the hardened body.

16. A method comprising using the composition of claim 1 as a dental material.

17. A method comprising using the composition of claim 9, as a dental coating material.

18. A method comprising using the composition of claim 10, as a dental cement.

19. A method comprising using the composition of claim 11, as a dental filling material.

* * * * *

UNITED STATES PATENT AND TRADEMARK OFFICE
CERTIFICATE OF CORRECTION

PATENT NO. : 7,595,354 B2
APPLICATION NO. : 11/338034
DATED : September 29, 2009
INVENTOR(S) : Moszner et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 822 days.

Signed and Sealed this

Twenty-eighth Day of September, 2010

David J. Kappos
*Director of the United States Patent and Trademark Office*